(12) United States Patent  (10) Patent No.: US 8,331,742 B2
Taverner et al.  (45) Date of Patent: *Dec. 11, 2012

(54) EVANESCENT SENSOR USING A HOLLOW-CORE RING MODE WAVEGUIDE

(75) Inventors: Domino Taverner, Delray Beach, FL (US); Edward M. Dowd, Madison, CT (US)

(73) Assignee: Weatherford/Lamb, Inc., Houston, TX (US)

( * ) Notice: Subject to any disclaimer, the term of this patent is extended or adjusted under 35 U.S.C. 154(b) by 138 days.

This patent is subject to a terminal disclaimer.

(21) Appl. No.: 12/710,147

(22) Filed: Feb. 22, 2010

(65) Prior Publication Data

US 2010/0150497 A1 Jun. 17, 2010

Related U.S. Application Data

(63) Continuation of application No. 11/551,853, filed on Oct. 23, 2006, now Pat. No. 7,668,419.

(51) Int. Cl.
*G02B 6/00* (2006.01)
(52) U.S. Cl. ............................................. 385/13; 385/12
(58) Field of Classification Search ...................... 385/12
See application file for complete search history.

(56) References Cited

U.S. PATENT DOCUMENTS

| | | | |
|---|---|---|---|
| 3,819,250 A | 6/1974 | Kibler | |
| 4,201,446 A | 5/1980 | Geddes et al. | |
| 5,319,435 A | 6/1994 | Melle et al. | |
| 5,945,666 A | 8/1999 | Kersey et al. | |
| 6,269,207 B1 | 7/2001 | Carberry et al. | |
| 6,836,606 B2 | 12/2004 | Abeeluck et al. | |
| 7,016,586 B2 | 3/2006 | Zoorob et al. | |
| 7,409,133 B2 | 8/2008 | Dimmick et al. | |
| 7,668,419 B2 * | 2/2010 | Taverner et al. | 385/30 |
| 2004/0179765 A1 * | 9/2004 | Kersey et al. | 385/12 |

FOREIGN PATENT DOCUMENTS

| | | |
|---|---|---|
| GB | 2037448 | 7/1980 |
| GB | 2190741 | 11/1987 |
| WO | 9735220 | 9/1997 |

OTHER PUBLICATIONS

Olivier Parriaux et al., "Normalized Analysis for the Sensitivity Optimization of Integrated Optical Evanescent-Wave Sensors," Journal of Lightwave Technology, Apr. 1998, vol. 16(4): pp. 573-582.

(Continued)

*Primary Examiner* — Omar Rojas
(74) *Attorney, Agent, or Firm* — Patterson & Sheridan, LLP

(57) ABSTRACT

Method and apparatus enable optical evanescent sensing utilizing a waveguide with an annular core. The annular core can provide detectable sensitivity to a measurand due to optical interactions with contents along an inside surface of the annular core since optical properties of the contents vary with changes in the measurand.

16 Claims, 4 Drawing Sheets

OTHER PUBLICATIONS

Ainhoa Gaston et al., "Evanescent Wave Optical-Fiber Sensing (Temperature, Relative Humidity, and pH Sensors)," IEEE Sensors Journal, Dec. 2003, vol. 3(6): pp. 806-811.

Kyunghwan Oh et al., "Novel Hollow Optical Fibers and Their Applications in Photonic Devices for Optical Communications," Journal of Llghtwave Technology, Feb. 2005, vol. 23(2): pp. 524-532.

Athanasios N. Chryssis et al., "High Sensitivity Evanescent Field Fiber Bragg Grating Sensor," IEEE Photonics Technology Letters, Jun. 2005, vol. 17(6): pp. 1253-1255.

Sameer M. Chandani et al., "Fiber-Optic Temperature Sensor using Evanescent Fields in D Fibers," IEEE Photonics Technology Letters, Dec. 2005, vol. 17(12): pp. 2706-2708.

British Search Report for Application No. GB0720602.2 dated Jan. 29, 2008.

Office Action dated Apr. 24, 2012 issued by the Canadian Intellectual Property Office in Application No. 2,606,662.

* cited by examiner

EVANESCENT SENSOR USING A HOLLOW-CORE RING MODE WAVEGUIDE

CROSS-REFERENCE TO RELATED APPLICATION

This application is a continuation of U.S. patent application Ser. No. 11/551,853 filed Oct. 23, 2006, now U.S. Pat. No. 7,668,419 which is incorporated by reference herein.

BACKGROUND OF THE INVENTION

1. Field of the Invention

Embodiments of the invention generally relate to an optical evanescent sensor utilizing a waveguide with an annular core.

2. Description of the Related Art

Various applications utilize optical sensors to measure parameters such as temperatures, pressures, biological compounds and chemicals in a particular environment. For example, uses of optical sensors include industrial sensing, research, medical analysis, and oil/gas recovery operations such as those occurring in a wellbore. These optical sensors can provide enhanced sensitivity, geometrical flexibility, miniaturization, durability in harsh environments with high temperatures and/or pressures, immunity from electromagnetic interference and multiplexing capabilities.

Some optical sensors function as evanescent sensors based on detection of changes in light propagating through an optical waveguide due to the optical mode penetrating evanescently into a surrounding media sensitive to a parameter being sensed. Techniques for producing evanescent sensors can rely on etching or polishing one side of an optical waveguide to produce a "D" shaped sensing element that brings the propagating mode along an interaction area in close proximity to the flat side such that a significant evanescent field is produced. However, long and complicated processes required to produce these sensing elements make such devices expensive. Further, the polishing or etching techniques used to produce the sensing element impose practical limits on a length of the interaction area that can be achieved since, for example, side-polished fiber portions are generally only a few millimeters long.

Therefore, there exists a need for an improved evanescent optical sensor that is easy to manufacture. A further need exists for a simple, flexible, monolithic, highly sensitive optical sensor element, which can be coupled to standard single mode optical fiber.

SUMMARY OF THE INVENTION

Embodiments of the invention generally relate to optical evanescent sensors utilizing a waveguide with an annular core. For some embodiments, the annular core provides detectable sensitivity to a measurand due to optical interactions, that vary in response to changes with the measurand, with contents along an inside surface of the annular core.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention generally relate to optical evanescent sensors utilizing a waveguide with an annular core. Various applications can utilize these sensors to measure parameters such as temperatures, pressures, biological compounds and chemicals in a particular environment. For example, uses of the sensors described herein include industrial sensing, research, medical analysis, and oil/gas recovery operations such as those occurring in a wellbore. For some embodiments, the annular core provides detectable sensitivity to a measurand due to optical interactions, that vary respectively with changes in the measurand, with contents along an inside surface of the annular core.

Figure 1:
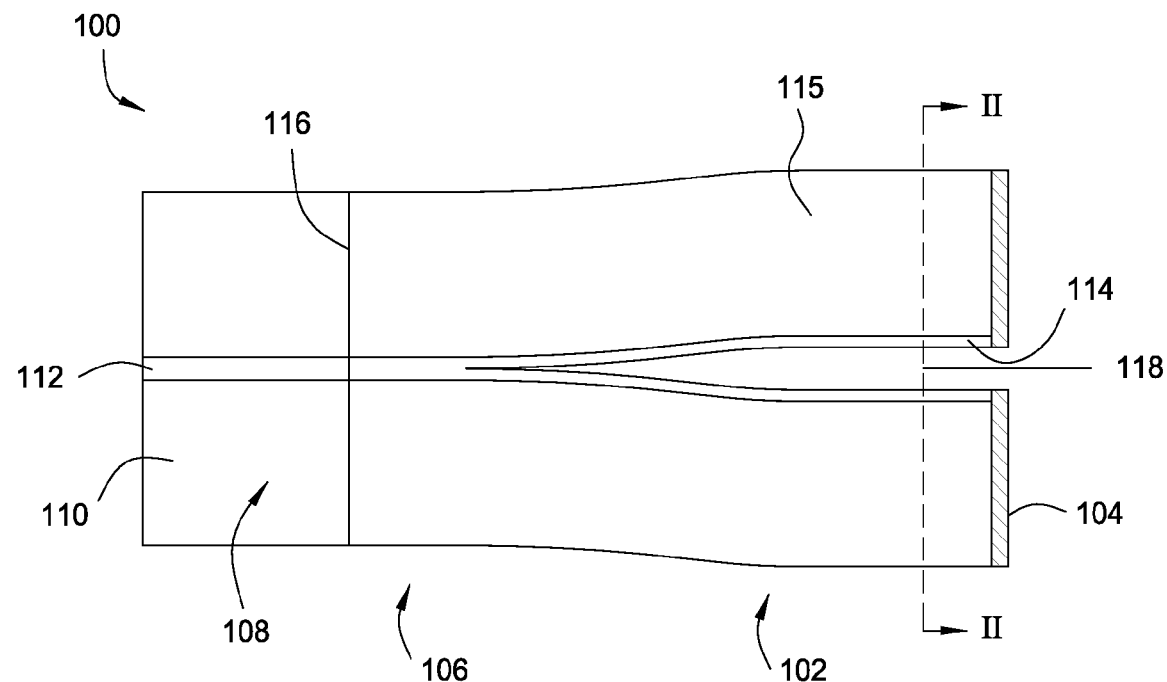
FIG. 1 is a schematic section view of a sensing element, according to embodiments of the invention, defined by a hollow-core ring mode waveguide with mirrored end facet and collapsed end shown spliced to a transmission waveguide.
Figure 7:
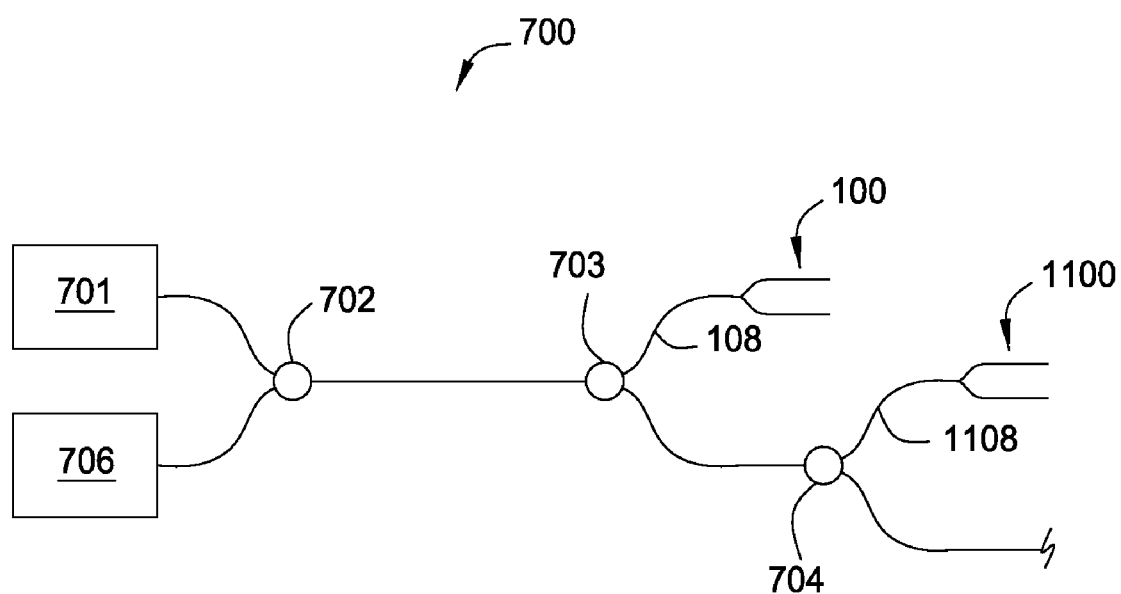
FIG. 7 is a schematic sensor system utilizing the sensing elements, according to embodiments of the invention.

FIG. 1 shows a sensing element 100 for use with appropriate components such as shown in FIG. 7 to enable measuring of a parameter or measurand at the sensing element 100. The sensing element 100 includes a hollow-core ring mode waveguide section 102 with mirrored end facet 104 and collapsed end section 106 coupled to a transmission waveguide 108. The hollow-core ring mode waveguide section 102 of the sensing element 100 defines an annular core 114 surrounded by a cladding 115. An interior volume 118 inside of the annular core 114 provides sensitivity to a measurand as described in detail herein. The hollow-core ring mode waveguide section 102 transitions to the collapsed end section 106 in a manner that provides adiabatic mode transformation to convert with low loss (e.g., 0.3 dB) ring mode(s) propagating along the annular core 114 to conventional linear mode(s). A fusion splice 116 coupling the sensing element 100 at the collapsed end section 106 with the transmission waveguide 108 can thereby be achieved with a standard optical fiber splicer.

The transmission waveguide 108 includes a cladding portion 110 disposed around a central core 112 such that the transmission waveguide 108 can define a single-mode optical pathway for coupling interrogating light in and out of the sensing element 100.

Figure 2:
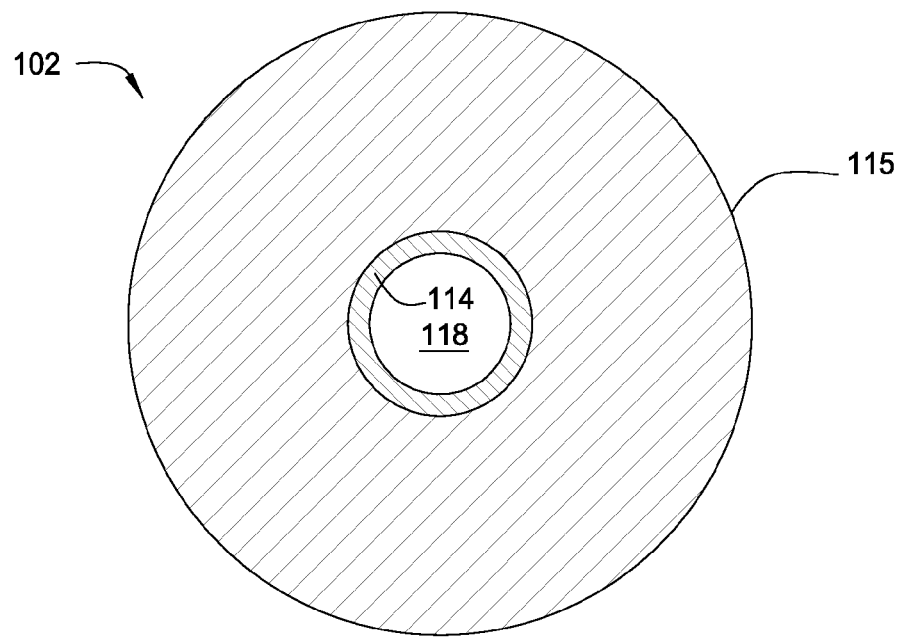
FIG. 2 is cross-section view of the sensing element shown in FIG. 1 taken across line II-II.

FIG. 2 illustrates a cross-section view of the sensing element 100 taken across line II-II in FIG. 1. The cladding 115 bounds along the outside of the annular core 114 the optical field within the annular core 114. Further, contents of the interior volume 118 bound along the inside surface of the annular core 114 the optical field such that a significant evanescent field is present in the interior volume 118. For some embodiments, air/gas/liquid/solid/vacuum fills the interior volume 118 such that a "hollow" portion of the hollow-core ring mode waveguide section 102 may or may not be empty.

Figure 3:
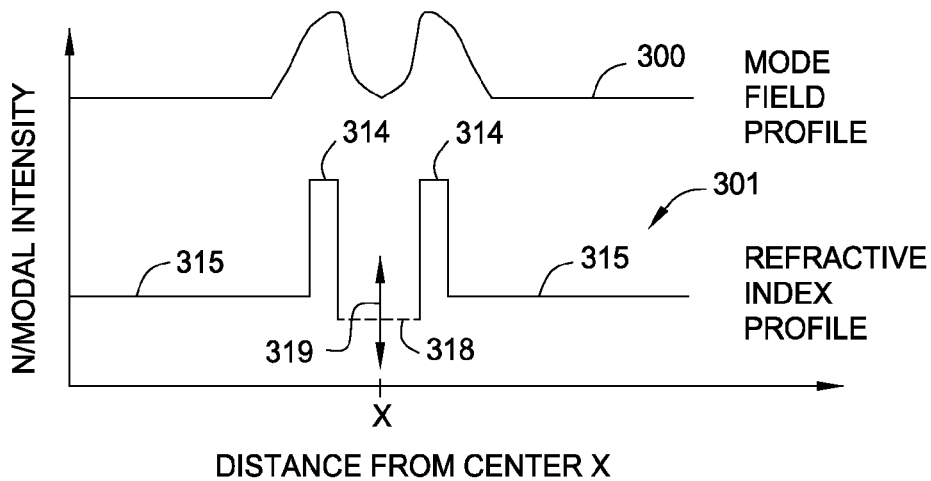
FIG. 3 is a plot of mode field profile and refractive index profile through the hollow-core ring mode waveguides of the invention.

FIG. 3 shows a plot of mode field profile 300 and refractive index (n) profile 301 across a section, such as shown in FIG. 2, of the hollow-core ring mode waveguide section 102. A core refractive index 314 relatively higher than a cladding refractive index 315 confines and guides the optical mode along the annular core 114 as depicted by the mode field profile 300. Further, the mode field profile 300 illustrates the evanescent field present within the interior volume 118, which has a content refractive index 318 that, for some embodiments, varies as indicated by arrow 319 in response to changes in the measurand.

The evanescent field present in at least a portion of the interior volume 118 can allow interaction with at least a portion of the contents of the interior volume 118 along an entire length of the hollow-core ring mode waveguide section 102 in order to provide sensitivity to properties of the contents within the interior volume 118. For example, these properties dependent on the measurand can include absorption or refractive index. Changes in such properties as a direct result of the measurand or otherwise in response to the measurand affect the wave-guiding properties, such as loss, through the annular core 114. Detection of these affects with signal processing equipment 706 (shown in FIG. 7) optically coupled to the transmission waveguide 108 provides an indicative assessment of the measurand. For example, changes in the refractive index of contents within the interior volume 118 can either maintain the light propagating in the annular core 114 or cause the light to leave the annular core 114 as a result of the difference in refractive indices between the annular core 114 and the contents of the interior volume 118. As a result, measuring attenuation of a response signal corresponds to the refractive index of contents within the interior volume 118 and thereby enables measurement of the parameter that caused the change in refractive index of the contents within the interior volume 118.

The sensing element 100 can be formed by any suitable methods. For example, production of the sensing element 100 can be based on conventional silica fiber manufacturing techniques and include fabrication of a preform and then drawing of the preform to provide a hollow optical waveguide. In practice, a doped core layer can be deposited inside a fused quartz substrate tube to provide the preform. Partial collapse of the preform occurs during waveguide drawing while maintaining a central air hole intact along the axial direction. Control over temperature, drawing tension, and/or positive pressure along the air hole can provide manipulation of both the hole diameter across the interior volume 118 and the thickness of the annular core 114, which may be selected to improve optical characteristics and/or tailor these characteristics based on the measurand, environment, sensor configuration, and application to achieve greater detectable changes. The hollow optical waveguide once produced can be locally heated to collapse in a tapered manner the hollow optical waveguide to form a solid core and thereby at least substantially match the transmission waveguide 108 at the collapsed end section 106.

In use as a sensor, the sensing element 100 couples to the transmission waveguide 108, which couples light from a source 701 (shown in FIG. 7) into and out of the sensing element 100. The mirrored end facet 104 can include a coating of a metal or thin-film mirror that reflects the propagating optical mode. This reflected light provides a signal from the sensing element 100 that is detected by the signal processing equipment 706 (shown in FIG. 7). Termination of the hollow-core ring mode waveguide section 102 at the mirrored end facet 104 leaves the interior volume 118 open at this termination exposing the inside surface of the entire length of the annular core 114 to an environment being monitored.

Attenuation of the signal occurs due to absorption or coupling to other modes, which can be lossy. The contents of the interior volume 118, as provided from the environment, affect this signal attenuation based on the measurand. According to some embodiments, the measurand can be any physical/chemical quantity whose varying presence within the environment and hence the interior volume 118 corresponds to a change in, for example, refractive index of at least part of the interior volume 118. The level of attenuation correlates to the presence of the measurand and thus enables monitoring of the measurand.

Figure 4:
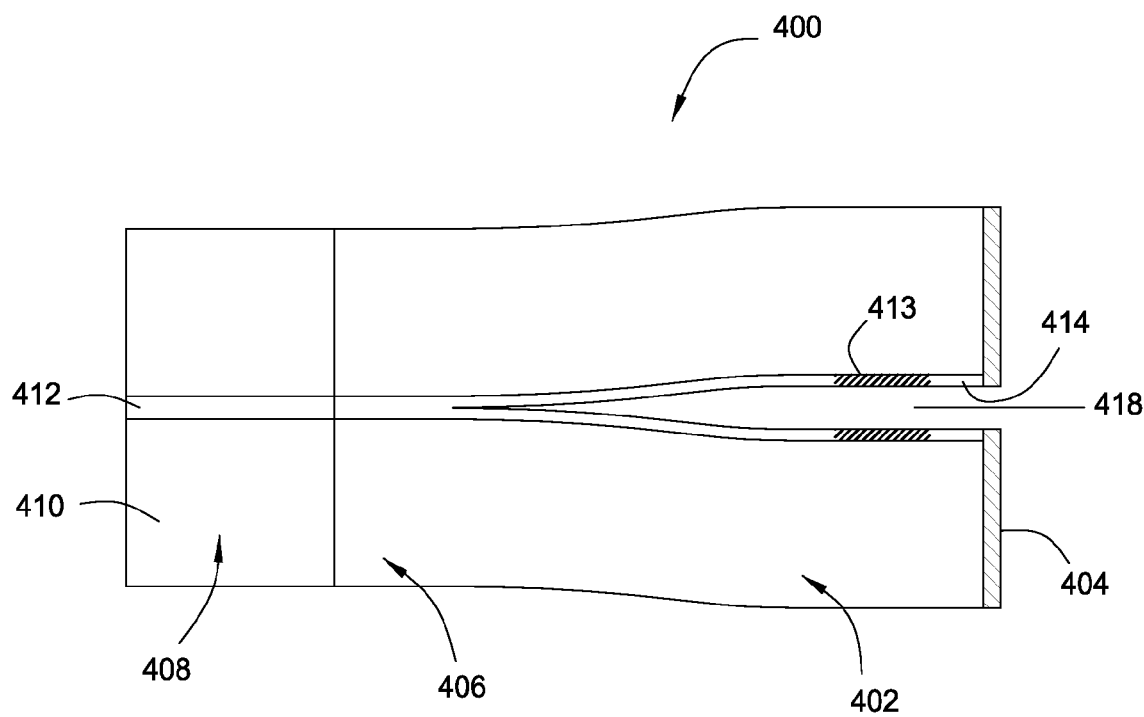
FIG. 4 is a schematic section view of a sensing element, according to embodiments of the invention, defined by a hollow-core ring mode waveguide with a grating reflector and collapsed end shown spliced to a transmission waveguide.

FIG. 4 illustrates a sensing element 400 defined by a hollow-core ring mode waveguide section 402 with a grating 413 and collapsed end section 406. The collapsed end section 406 enables optically coupling of the sensing element 400 to a network optical waveguide 408 having a cladding portion 410 around a central core 412. An annular core 414 of the sensing element 400 includes the grating 413, such as a short-period Bragg grating or a long-period Bragg grating (LPBG), written into the annular core 414. Some embodiments include an optional mirror coating 404 that is not required if the grating 413 is reflective. In embodiments where the grating 413 is the LPBG, the mirror coating 404 allows use of transmissive coupling of the grating 413 in a double-pass configuration.

The measurand can be any physical/chemical quantity whose varying presence in the interior volume 418 corresponds to a change in refractive index of contents within the interior volume 418. Based on the measurand, the contents of the interior volume 418 affect the wavelength of a feature such as a reflection peak or transmission trough in the optical spectrum of the grating 413, which is dependent on the refractive index. This wavelength change in returning signals can be monitored for assessing the measurand.

Termination of the hollow-core ring mode waveguide section 402 leaves the interior volume 418 open at this termination exposing the inside surface of the entire length of the annular core 414 to an environment being monitored. In embodiments where the grating 413 is the Bragg grating, a Bragg wavelength or peak wavelength of the reflected spectrum from the sensing element 400 shifts as the index of refraction of the contents within the interior volume 418 is changed around the annular core 414. As the surrounding refractive index of the contents within the interior volume 418 is increased and approaches the refractive index of the annular core 414, the Bragg wavelength increases with the rate of increase, which defines sensitivity, also intensifying. Signal processing equipment can detect this change in the Bragg wavelength thereby providing an assessment of the measurand.

As an exemplary application for the sensing element 400, the contents of the interior volume 418 may contain glucose that can provide an index of refraction change of $2.5 \times 10^{-5}$ per milli-Molar change in concentration of glucose corresponding to a detectable change (e.g., 35 picometer) in Bragg wavelength. Similarly, the LPBG used as the grating 413 can produce resonance shifts of transmission troughs in response to changes in sugar concentration. Other calibrations between refractive index changes and other chemical/biochemical concentrations can be made for applications with different measurands.

Configuration of the hollow-core ring mode waveguide section 402 exposes the inside surfaces of the annular core 414 such that polishing or etching is not required to remove any cladding layers. However, etching some of the annular core 414 can increase sensitivity. This increase in sensitivity can result from larger shifts being produced by the grating 413 disposed in the annular core 414.

Figure 5:
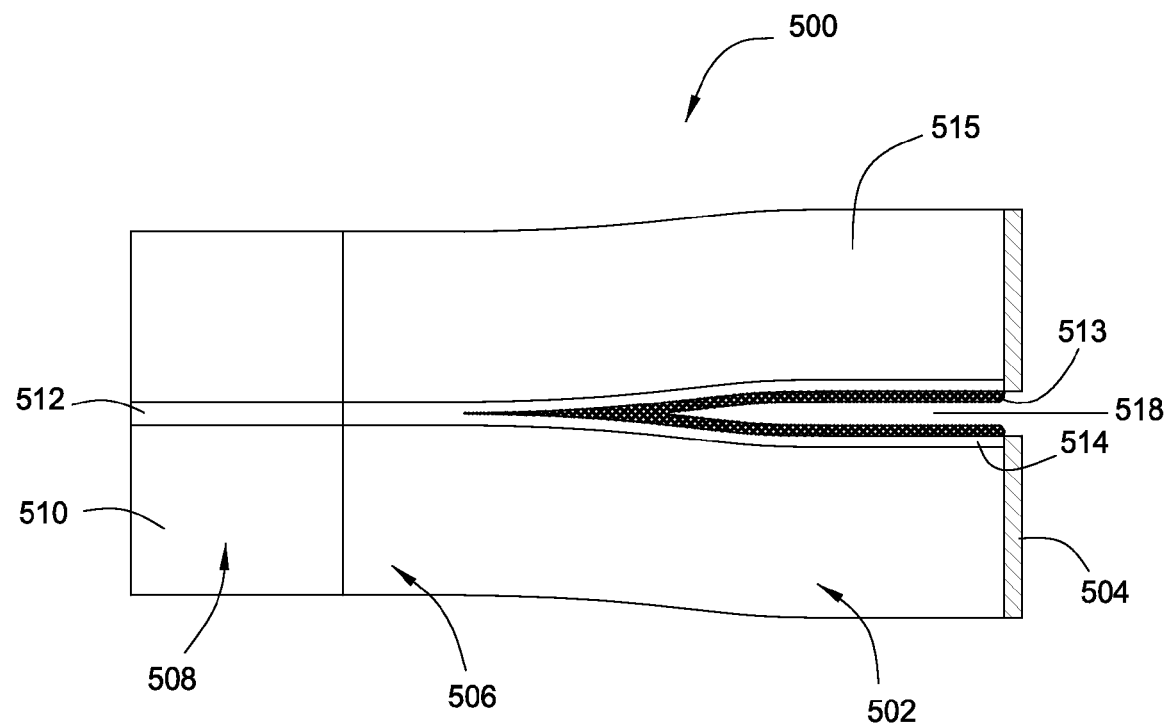
FIG. 5 is a schematic section view of a sensing element, according to embodiments of the invention, defined by a hollow-core ring mode waveguide with a coated inner sensing surface and a collapsed end shown spliced to a transmission waveguide.

FIG. 5 shows a sensing element 500 with a responsive layer of material or coating 513 disposed along an inner sensing surface of an annular core 514. The sensing element 500 represents any of the sensing elements having different aspects as described herein with the coating 513 mediating or assisting the sensing process as the evanescent field penetrates the coating 513. As a typical generic basis, a reflective member 504 returns a response signal generated in a hollow-core ring mode waveguide section 502 toward a collapsed end section 506 coupled to a network optical waveguide 508 having a cladding portion 510 around a central core 512.

The coating 513 provides sensitivity to certain desired measurands (e.g., hydrogen, magnetic fields, electric fields, humidity, other chemicals, temperature and/or photonics). For some embodiments, the coating 513 changes its refractive index in response to the measurand. The change in the refractive index of the coating 513 can occur with changes in temperature, application of an electric field, an infusion of a chemical compound, changes in pressure and/or any other change in environmental conditions in relation to the measurand of interest. Changes in the refractive index of the coating 513 affect the propagation of the light within the sensor 500.

The refractive index of the coating 513 can change with temperature for the most part proportionally with changes in the density of the coating 513 caused by an increase in volume of a polymer making up the coating 513. The refractive index increases due to a decrease in volume as the coating 513 cools, and the refractive index decreases due to an increase in volume as the coating 513 heats up. The change in refractive index of the coating 513 based on changes in temperature can be used in two ways. The coating 513 may have a refractive index slightly higher than a cladding 515 at room temperature (approximately 24° C) such that the coating 513 acts as a mode stripper at room temperature and effectively strips light from the sensor 500. As the temperature increases and the refractive index of the coating 513 decreases to the refractive index of the cladding 515, the coating 513 acts as cladding and reflects the light into the senor 500. Examples of polymers with this refractive index characteristic that can be used as the coating 513 include copolymers of polydimethyldiphenysiloxane. Alternatively, the polymer coating 513 may be made from a polymer having a lower refractive index than the refractive index of the cladding 515 at room temperature. Thus, the light transmits through the sensor 500 at room temperature but not at lower temperatures. Polymers meeting these criteria for refractive index include polydimethylsiloxane and highly fluorinated hydrocarbons such as polyperfluorocyclohexylacrylate. Thus, measuring the changes in total optical light output or intensity that is either transmitted directly through the sensor 500 or reflected back provides a quantitative and qualitative indication of the temperature of the coating 513 and hence the temperature of the environment surrounding the coating 513.

The previous two examples provided illustrate the use of particular polymers as the coating 513 to enable the determination of an increase or decrease in temperature from a given temperature such as room temperature. As a further example, the coating 513 can include a thin solid film of polyvinyl alcohol (PVA), which has varying absorption with humidity. The coating 513 thus selected provides a higher refractive index than the annular core 514 when dry such that optical modes in essence propagate through a region with a lossy cladding. However, exposing the coating 513 to water or humidity causes the PVA to swell due to hydrogen bond formation with water thereby reducing the refractive index. This reduction in refractive index reduces the evanescent field penetration inducing attenuation that can be detected and correlated to the humidity.

For pH measurements with the sensor 500, the coating 513 can include a sol-gel material doped with an optical indicator such that the coating 513 has a varying attenuation with pH. A preparation utilizing tetraethyl orthosilicate (TEOS) doped with eriochrome cyanine R can provide an exemplary basis for the coating 513 according to such an embodiment. Attenuation can be detected and correlated to the pH.

Figure 6:
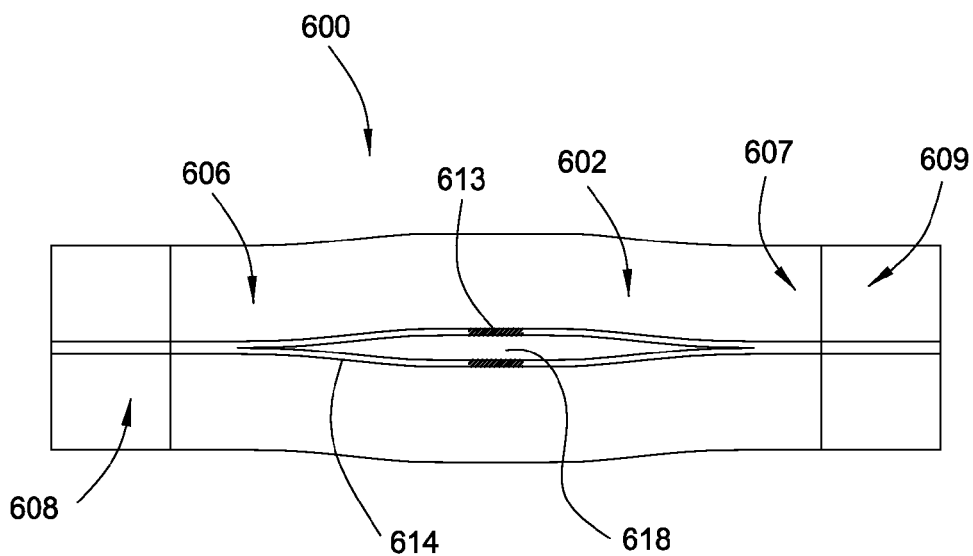
FIG. 6 is a schematic section view of a sensing element, according to embodiments of the invention, defined by a hollow-core ring mode waveguide with a grating reflector and two collapsed ends shown spliced within a transmission waveguide.

FIG. 6 illustrates a sensing element 600 defined by a hollow-core ring mode waveguide section 602 having an interior volume 618 that is sealed. While the interior volume 618 is shown sealed due to first and second collapsed end sections 606, 607, other closing structures or caps can replace one of the collapsed end sections 606, 607 if not desired to configure the sensing element 600 as a pass-through sensor, which enables multiple sensing elements to be cascaded. In practice, any of the embodiments described herein can operate with the interior volume sealed thereby permanently trapping any contents in the interior volume if the environmental property to be studied does not require direct contact with the annular core. During operation, a Bragg grating 613 returns a response signal generated in a hollow-core ring mode waveguide section 602 towards a first waveguide 608 coupled to the first collapsed end 606 while a portion of the incoming light can pass through to a second waveguide 609 for interrogation by other sensing elements.

Temperature represents one measurand that does not require direct contact with the annular core 614. As previously discussed, a coating along the inside surface of the annular core 614 can make the sensor 600 responsive to temperature changes in the environment that the sensing element 600 is disposed in even though the interior volume 618 is sealed. Furthermore, the interior volume 618 can contain oil with temperature varying refractive indices. The oil sealed inside of the interior volume 618 and in contact with the inside of the annular core 614 couples light out of the guided mode to selectively cause attenuation based on the temperature of the oil. The temperature of the oil assumes the temperature of the environment around the sensing element 600 enabling temperature sensing by measuring the attenuation.

FIG. 7 shows an exemplary sensor system 700 utilizing the sensing element 100 within an optical network. The system 700 includes the source 701, the processing equipment 706, the transmission waveguide 108, the sensing element 100, and one or more circulators 702, 703, 704 or splitters. Further, the system 700 can include an additional sensing element 1100, such as those described herein, and any number of further sensing elements. The additional sensing element 1100 connects to an additional transmission waveguide 1108 that integrates the sensing element 1100 into the network. In operation, the circulators 702, 703, 704 direct the light from the source 701 to the sensing elements 100, 1100 and the return signals from the sensing elements 100, 1100 to the processing equipment 706 for detection and/or analysis based on the description heretofore.

While the foregoing is directed to embodiments of the present invention, other and further embodiments of the invention may be devised without departing from the basic scope thereof, and the scope thereof is determined by the claims that follow.

The invention claimed is:

1. An optical sensor element for measuring a parameter, comprising:
    a hollow-core ring mode waveguide section having an annular core with an inner surface defining an interior volume;
    a coating disposed adjacent the inner surface of the annular core and filling only a portion of the interior volume, wherein the coating is responsive to the parameter; and
    first and second collapsed end sections sealing the interior volume of the hollow-core ring mode waveguide section, wherein each of the collapsed end sections transitions from the hollow-core ring mode waveguide section and includes a solid core.

2. The optical sensor element of claim 1, wherein the annular core comprises at least one grating.

3. The optical sensor of claim 2, wherein a reflection wavelength of the grating is responsive to the parameter.

4. The optical sensor element of claim 2, wherein the at least one grating comprises at least one long-period Bragg grating (LPBG) written into the annular core.

5. The optical sensor element of claim 1, further comprising oil disposed in the sealed interior volume.

6. The optical sensor element of claim 5, wherein a refractive index of the oil changes in response to variance in the parameter.

7. The optical sensor element of claim 6, wherein the parameter comprises temperature.

8. An optical sensing apparatus for measuring at least one parameter, comprising:
    a first optical sensor element, comprising:
        a hollow-core ring mode waveguide section having an annular core with an inner surface defining an interior volume;
        a coating disposed adjacent the inner surface of the annular core and filling only a portion of the interior volume, wherein the coating is responsive to the parameter; and
        first and second collapsed end sections sealing the interior volume of the hollow-core ring mode waveguide section, wherein each of the collapsed end sections transitions from the hollow-core ring mode waveguide section and includes a solid core; and
    a second optical sensor element coupled to the second collapsed end section such that at least a portion of incoming light received at the first collapsed end section of the first optical sensor element passes through to the second optical sensor element.

9. The optical sensing apparatus of claim 8, wherein the annular core comprises a grating.

10. The optical sensing apparatus of claim 8, wherein the first and second optical sensor elements are coupled by an optical waveguide having a solid core surrounded by a cladding.

11. The optical sensing apparatus of claim 8, wherein the second optical sensor element comprises:
    a second hollow-core ring mode waveguide section having an annular core with an inner surface defining an interior volume; and
    third and fourth collapsed end sections sealing the interior volume of the second hollow-core ring mode waveguide section, wherein each of the third and fourth collapsed end sections transitions from the second hollow-core ring mode waveguide section and includes a solid core.

12. The optical sensing apparatus of claim 8, wherein the second optical sensor element comprises:
    a second hollow-core ring mode waveguide section having an annular core with an inner surface defining an interior volume and having a mirrored end facet, wherein at least part of the inner surface forms a parameter-sensitive optical interaction area; and
    a third collapsed end section that transitions from the second hollow-core ring mode waveguide section and includes a solid core.

13. The optical sensing apparatus of claim 8, wherein the coating changes refractive index in response to the parameter.

14. The optical sensing apparatus of claim 8, wherein the coating comprises at least one of polydimethyldiphenysiloxane or polyperfluorocyclohexylacrylate.

15. The optical sensor element of claim 1, wherein the coating changes refractive index in response to the parameter.

16. The optical sensor element of claim 1, wherein the coating comprises at least one of polydimethyldiphenysiloxane or polyperfluorocyclohexylacrylate.

* * * * *

UNITED STATES PATENT AND TRADEMARK OFFICE
CERTIFICATE OF CORRECTION

PATENT NO.         : 8,331,742 B2
APPLICATION NO.    : 12/710147
DATED              : December 11, 2012
INVENTOR(S)        : Taverner et al.

It is certified that error appears in the above-identified patent and that said Letters Patent is hereby corrected as shown below:

Title Page 2, Column 2, line 8, References Cited (56):
Please insert --X. CHEN et al., "Optical Chemsensors Utilizing Long-Period Fiber Gratings UV-Inscribed in D-Fiber with Enhanced Sensitivity through Cladding Etching," IEEE Photonics Technology Letters, May 2004, Vol. 16(5): pp.1352-1354.--.

Signed and Sealed this
Sixth Day of August, 2013

Teresa Stanek Rea
*Acting Director of the United States Patent and Trademark Office*